(12) United States Patent
Fabry

(10) Patent No.: US 9,643,896 B2
(45) Date of Patent: *May 9, 2017

(54) DUAL PURPOSE AGRICULTURAL COMPOSITIONS

(71) Applicant: Plant Food Systems, Inc., Zellwood, FL (US)

(72) Inventor: Carl Fabry, Orlando, FL (US)

(73) Assignee: Plant Food Systems, Inc., Zellwood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/049,456

(22) Filed: Feb. 22, 2016

(65) Prior Publication Data

US 2016/0185681 A1    Jun. 30, 2016

Related U.S. Application Data

(60) Continuation of application No. 14/696,977, filed on Apr. 27, 2015, now Pat. No. 9,266,788, which is a continuation of application No. 13/912,340, filed on Jun. 7, 2013, now Pat. No. 9,056,803, which is a continuation of application No. 13/538,661, filed on Jun. 29, 2012, now Pat. No. 8,461,079, which is a continuation of application No. 13/035,959, filed on Feb. 26, 2011, now abandoned, said application No. 13/912,340 is a continuation-in-part of application No. 13/094,932, filed on Apr. 27, 2011, now Pat. No. 8,216,972, which is a continuation-in-part of (Continued)

(51) Int. Cl.
| | | |
|---|---|---|
| C05D 9/00 | (2006.01) |
| C05D 9/02 | (2006.01) |
| C05C 11/00 | (2006.01) |
| A01N 59/26 | (2006.01) |
| C05G 3/02 | (2006.01) |
| C05B 13/00 | (2006.01) |
| C05B 17/00 | (2006.01) |
| C05G 3/00 | (2006.01) |
| A01N 37/40 | (2006.01) |

(52) U.S. Cl.
CPC ............... *C05G 3/02* (2013.01); *A01N 37/40* (2013.01); *A01N 59/26* (2013.01); *C05B 13/00* (2013.01); *C05B 17/00* (2013.01); *C05G 3/0064* (2013.01)

(58) Field of Classification Search
CPC .............. C05G 3/02; A01N 59/26; C05B 7/00
USPC ................. 71/34, 35, 41, 48, 49, 50, 54, 58; 504/101
See application file for complete search history.

(56) References Cited

U.S. PATENT DOCUMENTS 3,796,595 A * 3/1974 David .................... A01N 57/14
162/161
5,736,164 A * 4/1998 Taylor .................... A01N 57/12
424/601

(Continued)

*Primary Examiner* — Stanley Silverman
*Assistant Examiner* — Syed Iqbal
(74) *Attorney, Agent, or Firm* — Christopher M. Ramsey; GrayRobinson, P.A.

(57) ABSTRACT

A method of fertilizing a plant comprises applying to a plant an effective amount of a composition comprising a product of a salicylic acid, a potassium polyphosphite, a potassium phosphite, and a potassium phosphate. The composition may be prepared by reacting salicylic acid, ammonium hydroxide, potassium hydroxide and/or potassium carbonate, phosphoric acid, and phosphorous acid.

21 Claims, 5 Drawing Sheets

Related U.S. Application Data application No. 13/035,779, filed on Feb. 25, 2011, now Pat. No. 8,193,119, said application No. 13/912,340 is a continuation-in-part of application No. 13/544,064, filed on Jul. 9, 2012, now Pat. No. 8,585,796, which is a continuation of application No. 13/308,681, filed on Dec. 1, 2011, now Pat. No. 8,221,516, which is a division of application No. 13/019,564, filed on Feb. 2, 2011, now Pat. No. 8,088,191, which is a division of application No. 11/349,064, filed on Feb. 6, 2006, now Pat. No. 7,887,616.

(60) Provisional application No. 61/308,598, filed on Feb. 26, 2010, provisional application No. 61/308,569, filed on Feb. 26, 2010, provisional application No. 60/650,378, filed on Feb. 4, 2005.

(56) References Cited

U.S. PATENT DOCUMENTS

| | | | |
|---|---|---|---|
| 8,076,266 B2* | 12/2011 | Dean | A01N 59/04 504/100 |
| 2004/0035162 A1* | 2/2004 | Williams | C05B 17/00 71/28 |

* cited by examiner

DUAL PURPOSE AGRICULTURAL COMPOSITIONS

CROSS-REFERENCE TO RELATED APPLICATIONS

This is a continuation of application Ser. No. 14/696,977, filed Apr. 27, 2015, now U.S. Pat. No. 9,266,788, which is a continuation of application Ser. No. 13/912,340, filed on Jun. 7, 2013, which is a continuation of application Ser. No. 13/538,661, filed on Jun. 29, 2012, now U.S. Pat. No. 8,461,079, which is a continuation of application Ser. No. 13/035,959, filed on Feb. 26, 2011 and claims the benefit of provisional Application No. 61/308,598, filed on Feb. 26, 2010. Application Ser. No. 13/912,340 is also a continuation-in-part of application Ser. No. 13/094,932, filed on Apr. 27, 2011, now U.S. Pat. No. 8,216,972, which is a continuation-in-part of application Ser. No. 13/035,779, filed on Feb. 25, 2011, now U.S. Pat. No. 8,193,119, which claims the benefit of provisional Application No. 61/308,569, filed on Feb. 26, 2010. Application Ser. No. 13/912,340 is also a continuation-in-part of application Ser. No. 13/544,064, filed on Jul. 9, 2012, now U.S. Pat. No. 8,585,796, which is a continuation of application Ser. No. 13/308,681, filed on Dec. 11, 2011, now U.S. Pat. No. 8,221,516, which is a division of application Ser. No. 13/019,564, filed on Feb. 2, 2011, now U.S. Pat. No. 8,088,191, which is a division of application Ser. No. 11/349,064, filed on Feb. 6, 2006, now U.S. Pat. No. 7,887,616, which claims the benefit of provisional Application No. 60/650,378, filed on Feb. 4, 2005. Each of these prior applications is incorporated by reference in its entirety.

FIELD

The present disclosure relates to agricultural treatments, and more specifically to pesticidal and nutritional application.

BACKGROUND

Plants are subject to a wide variety of fungal and bacterial diseases and damage by insects. Fruit bearing plants, in particular citrus trees are subject severally totally destructive diseases, *Xanthomonas axonopodis* pv. *Citri* (Xac), Asiatic citrus canker (Canker) and Huanglongbing/Citrus Greening (*Liberibacter asiaticus* (CGD), which is vectored by the Asian citrus psyllid (AsCP), *Diaphorina citri Kuwayama* (Greening).

Citrus canker and Greening are particular problems for citrus crops as is the insect vector, psyllids. Presently, Greening is prevalent worldwide throughout all the countries that produce citrus; there is no known cure. The official sometimes mandated, scientific worldwide recommendation is for trees identified and affected with Greening to be removed and burned. In the case of Canker, hundreds of thousands of acres worldwide have been destroyed and removed because of the effects of the disease. Presently the only official recommendation by the scientific community, is prophylactic by spraying surface protectants on the plant tissue of citrus trees, which has little or no because these surficial fungicidal sprays are easily washed off by moisture.

It would be desirable to have products that can be applied to fruit bearing plants that will systemically stop or effectively retard damage caused by fungal and bacterial diseases and insects while at the same time also fertilizing these plants and allowing the plants to rejuvenate while being healed and then continue to bear fruit, preferably in increased yields.

A one product "weed and feed" technology has long been available in the turf industry as a superior method to control weeds and promote plant growth; doing two jobs simultaneously and saving the cost of separate applications. If just a nutrient was applied separately to weed infested turf, both the turf and the weeds would benefit more than the turf. Likewise, if a costly second herbicide application was made applied separately the target weeds would be controlled but the grass would not grow quickly enough to outgrow the next crop of weeds.

Phosphorus (P) is one of the major elements required by all living species to grow and develop. When the element phosphorus is oxidized to the fullest extent possible, its acid is termed phosphoric acid, $[H_3PO_4$ or $PO(OH)_3]$, and the salts of phosphoric acid are termed phosphates, e.g. $K_2HPO_4$. With phosphorus in a slightly less oxidized form, the phosphorus in the acid form is termed phosphorous acid, $[H_3PO_3$, or $HPO(OH)_2]$, and the salts of phosphorous acid are termed phosphites, e.g. $K_2HPO_3$. Phosphites are marketed either as an agricultural fungicide, bactericide or without research data as a superior source of plant phosphorus (P) nutrition.

Polyphosphates are sometimes referred to as pyrophosphates. Additional phosphate ions may react further with the polyphosphate, $P_2O_7^{-4}$, to form longer polyphosphates and, in general, there is a mixture of varying polymer chain lengths in any given sample. The presence of some proportion of polyphosphates in fertilizer is useful for purposes of sequestration of impurities, as suspensions aids, and for making phosphorus more available to plants.

On the other hand, the lower valent phosphite $(PO_3^{-3})$, has never played an important role in the commercial fertilizer industry.

The analysis of polyphosphite content in a composition is difficult because all common wet chemical methods for determination of phosphite depend upon reagents that first convert phosphite to phosphate. These reagents will break up any polyphosphite molecules present in the composition into individual phosphite ions. Polyphosphite, therefore, cannot be detected or quantified by the routine wet chemical methods. For instance, iodine solutions are used to oxidize inorganic phosphites for subsequent analysis as phosphate. Iodine will breakup any phosphite polymer present and the polyphosphite will not be detected. Similarly, commercial labs which analyze fertilizers do not report phosphite levels but rather report them as phosphate. Also, during analytical procedures requiring heat, phosphites would typically be slowly converted to phosphate unless precautions are taken to prevent oxidation by excluding air. Furthermore, at elevated temperatures polyphosphates can be expected to hydrolyze to ordinary phosphite ion, analogously to the hydrolysis of polyphosphates under similar conditions. Accordingly, physical methods such as nuclear magnetic resonance (NMR), high pressure liquid chromatography (HPLC), liquid chromatography, mass spectrometry (MS), and other physical molecular weight determining methods are useful methods for characterizing polyphosphites.

NMR provides a unique method of detecting phosphite because in most cases, and particularly when in solution, it exists with a hydrogen attached to the phosphorus atom $(HPO_3^{-2})$.

Sophisticated NMR instruments, such as the Varian VXR-3005 spectrometer, can not only detect and measure $^{31}P$ but can also simultaneously perform measurements on atoms such as hydrogen attached to phosphorus or carbon by transfer polarization. Such an instrument can, therefore, detect and measure phosphite in the presence of other phosphorus species without ambiguity.

Potassium phosphite would be particularly useful because it would provide the second important nutrient of the three critical plant nutrients, potassium. Moreover, a polyphosphite can be expected to provide the sequestration and slow release advantages known with polyphosphate, although phosphites are more active fungicides.

Phosphites are highly selective, non-toxic fungicides active against numerous fungal pathogens, and provide both protective and curative responses against such plant disease isolates of *Phytophthora, Rhizoctonia, Pythium,* and *Fusarium,* and other plant diseases—but typically not against bacterial diseases. Additional information regarding phosphorus-based fertilizers is presented in the "Background of the Invention" section of U.S. Pat. No. 7,887,616, the contents of which are hereby incorporated by reference.

Current commercial methods for making salt compositions from phosphoric acid and phosphorous acid (Phosphorus (P) acids), for foliar application plants are described in the "Background of the Invention" section of U.S. Pat. No. 8,193,119, the contents of which are incorporated by reference.

SUMMARY

The invention discloses a pesticide and nutrient solution combination which will enhance plant growth more so than if each material is applied separately.

The novel composition of this invention comprises a blend of: (1) an aqueous salicylate solution; (2) an aqueous reaction mixture; and optionally, (3) an aqueous complexed potassium acetate solution.

The aqueous salicylate solution component (1) comprises salicylic acid reacted in an aqueous media with ammonium hydroxide and potassium hydroxide. It is well known that ammonium hydroxide and potassium hydroxide cannot be mixed together; otherwise an undesirable reaction will occur. In mixing with salicylic acid, it is first mixed with ammonium hydroxide, allowed to react and thereafter followed by addition of potassium hydroxide, or vice-versa.

The aqueous salicylate solution comprises 10-20% wt. salicylic acid substantially reacted in an aqueous media with a sufficient amount of between about 1 to 2 parts ammonium hydroxide and potassium hydroxide combined.

The aqueous reaction mixture component (2) is made from the reaction of: a) an acid solution comprising about 10-50 parts phosphorous acid and about 50-90 parts phosphoric acid; and, b) aqueous potassium hydroxide or ammonium hydroxide where the ratio of monovalent cations to phosphorus in mole rations is between about 1:1 to about 2:1. The reaction mixture formed comprises potassium phosphates, potassium polyphosphate, potassium phosphites, and potassium polyphosphite and potassium phosphate phosphite copolymers. 'The aqueous reaction mixture component (2) is blended under pressure in a continuous system such as a pipe reactor and thereafter rapidly cooled.

When an amount, concentration, or other values or parameters are given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

In the context of this disclosure, a number of terms are utilized.

The term "comprising" is intended to include embodiments encompassed by the terms "consisting essentially of" and "consisting of". Similarly, the term "consisting essentially of" is intended to include embodiments encompassed by the term "consisting of".

The term "potassium phosphate-phosphite copolymer(s)" means copolymers of potassium phosphates and potassium phosphites.

The term "aqueous potassium polyphosphite solution" means an aqueous mixture formed by the process of this invention wherein aqueous phosphorous acid is reacted with potassium hydroxide and comprises potassium ortho and polyphosphites, mono-potassium phosphite, and or di-potassium phosphite and forms a pesticidal and/or nutrient solution.

The term "reaction mixture" means an aqueous mixture formed by the process of this invention comprising potassium phosphate, potassium polyphosphates, potassium phosphite, potassium polyphosphites and potassium polyphosphate and polyphosphite copolymers.

The nutrients present, force quick vigorous growth of the crop, while enabling the crop to more effectively compete with pests held in check by the pesticide.

Plant spray compositions are disclosed that provide in one application fungicidal and/or bactericidal, and/or herbicidal and/or insecticidal protection to plants. Plant health is restored by providing foliar applied nutrients directly to the plants to provide energy for photosynthesis. This is beneficial particularly where root nutrient absorption has been comprised because of disease, chemical or mechanical plant injury or other environmental factors.

The combination of applying a pesticide with a nutrient solution synergistically enhances more growth than if each material is applied separately. The nutrients present force quick, vigorous growth of the crop, while enabling the crop to more effectively compete with pests held in check by the pesticide.

Because a concentrated acid solution is combined with a concentrated aqueous potassium hydroxide in a pipe reactor, this creates an exothermic reaction under pressure greater than atmospheric and results in a product comprising phosphates, polyphosphates, phosphites, polyphosphites and phosphate phosphite copolymers. Water is released as steam. Thereafter, the product is rapidly cooled to below 35° C. to about 65° C. to reduce the hydrolysis reaction or other degradation of the polyphosphates and polyphosphites formed. It is believed any excess water present will result in an undesired breakdown of the phosphate phosphite copolymers. Preservation of the polyphosphates, polyphosphites, and phosphate phosphite copolymers is critical because these components act respectively as a fertilizer and bactericide/fungicide when an effective amount of the reaction mixture is first diluted and then applied to plants. The process for making the reaction mixture is described in U.S. Pat. No. 8,216,972, the contents of which are incorporated by reference.

Optionally, aqueous complexed potassium acetate can be added to the blend of components (1) and (2).

When making the reaction mixture component (2), dry phosphorous acid can be dissolved directly into a concentrated liquid phosphoric acid to minimize wasteful "added free water", which would hinder the polymerizing reaction. Thus, a concentrated solution is formed having greater reactivity to form phosphorous acid polymers.

The phosphoric acid used can be in any commercial or practical concentration, usually from 75% to a 115% $H_3PO_4$ concentration. A concentration over 96% is considered to be super phosphoric acid; however, the preferred concentration is from 85% to 105% for practical commercial acid purchase availability, handling and storage advantage. The phosphorous solution can be in the range of 1-99 parts phosphoric acid to 99-1 parts phosphorous acid, preferably about 90-50 parts phosphoric acid to 10-50 parts phosphorous acid. The concentrated potassium hydroxide used is between about 40-60% wt.

An unexpected and important advantage of the process for forming a reaction product is that polyphosphate and polyphosphite can be prepared simultaneously. The presence of both acids in the process provides for the formation of copolymers, that is, polymers containing both phosphite and phosphate groups. Such copolymers are new materials and not simply a mixture of polyphosphite and polyphosphate. However, chemical analysis of such polymers is difficult.

Another aspect of the invention is a process for the application of an effective amount of each of the above components to plants, such as citrus plants or other fruit bearing plants, vegetable plants, turf and ornamental plants and field crops in order to provide fungicidal, bactericidal and insecticidal protection and fertilization to plants thereby improving yields.

The novel process of this invention provides a number of advantages over methods taught in the art. In a single step process, a fungicidal and fertilizer composition is prepared having polymeric components that have a higher analysis with long term storage stability allowing the composition to remain, as a clear solution, in storage for extended periods of time without "salting out", and remaining in a clear solution longer than conventionally produced orthophosphorous products. The polymerized products of this invention, and can be readily blended with other components, particularly sequestering inorganic metal compounds such as Copper, Iron, Manganese and Zinc to form higher analysis, stable compositions that reduce and many cases eliminate fungicidal activity on a wide variety of plants and crops and provides fertilizer components to plants and crops in particular, a polyphosphate which is well known to be beneficial to plants. Further, there is significantly less foliage burn caused when the products of this invention are applied directly to plants, because of the polymers present in the solutions of the invention. The polyphosphate and polyphosphite compounds of this invention are also capable of forming soluble complexes with metal impurities by a sequestration process; also, the compositions have activity as a pesticide.

An important aspect of the novel process, which has not been previously recognized, is that dissolving orthophosphorous acid directly in orthophosphoric or super polyphosphoric acid without additional of water provides a high concentration of highly reactive acid when used in the process is capable of producing polymeric compounds. Less water is present in the novel process thereby concentrating the acid favorably for the formation of polyphosphorus compounds. Thus, polymer formation is facilitated and increased and the exothermic reaction temperature is higher causing an additional release of water to provide a high concentration reaction mixture and conversion containing phosphate and phosphite polymers, along with residual ortho phosphate and ortho phosphite compounds. Further, degradation by hydrolysis of the potassium polyphosphites and related polymers is significantly reduced. With the use of a continuous reactor in the process, the risk of a "runaway" reaction is eliminated. The unwanted formation of phosphine gas that often occurs in a batch reaction, and which is very difficult to control, is eliminated by the complete, instantaneous reaction, and the rapid cooling process to below critical phosphine formation temperature levels. Only evaporative steam from the heat of reaction, and the dehydration of the phosphate and phosphite moieties in this novel process, is harmlessly discharged to the environment.

The aqueous reaction mixture component (2) of the present composition may also contain potassium phosphite and at least 25-75% by weight or more of potassium polyphosphite.

Additionally, described is a method of making a fungicidal composition having fertilizer properties and containing at least about 25-75% by weight of potassium polyphosphite. The method comprises reacting phosphorous acid and potassium hydroxide in aqueous solution at a temperature of at least approximately 270 F and rapidly cooling the aqueous solution to a temperature below approximately 90 F. A more preferred method includes making a composition consisting essentially of potassium polyphosphite by reacting phosphorous acid and potassium hydroxide in aqueous solution at a temperature above 270 F and rapidly cooling the aqueous solution to a temperature below approximately 90 F. The Method may be carried out wherein reacting is conducted at between about 300 F-350 F and wherein cooling is conducted at about 90 F or less.

The polyphosphite composition has fertilizer utility and a method of fertilizing a plant includes applying an effective amount of the composition. The present invention also includes a method of treating a plant for a fungal infection, the method comprising applying an effective amount of one of the polyphosphate compositions disclosed. The composition of the present invention may also be used for treating a plant for a microbial infection, that is, of an etiology other than a fungus, the method comprising applying an effective amount of the composition.

Moreover, the present polyphosphite composition has demonstrated effectiveness against bacterial diseases, including the bacterial plant pathogen, *Xanthomonas axonopodis* pv. *Citri* (Xac), which is the cause of Asiatic citrus canker, where no other cure is currently available.

In addition, *Ralstonia solanacearum*, a bacterial wilt infection, is virtually 100% controlled with the present polyphosphite composition. It has been discovered that a unique third mode of protection, is at work, in that control of the organism is by a previously unrecognized bacteriostatic method, rendering the pathogen unable to reproduce itself.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with the intent to limit the invention thereto, and in which.

DETAILED DESCRIPTION OF EMBODIMENTS

Figure 1:
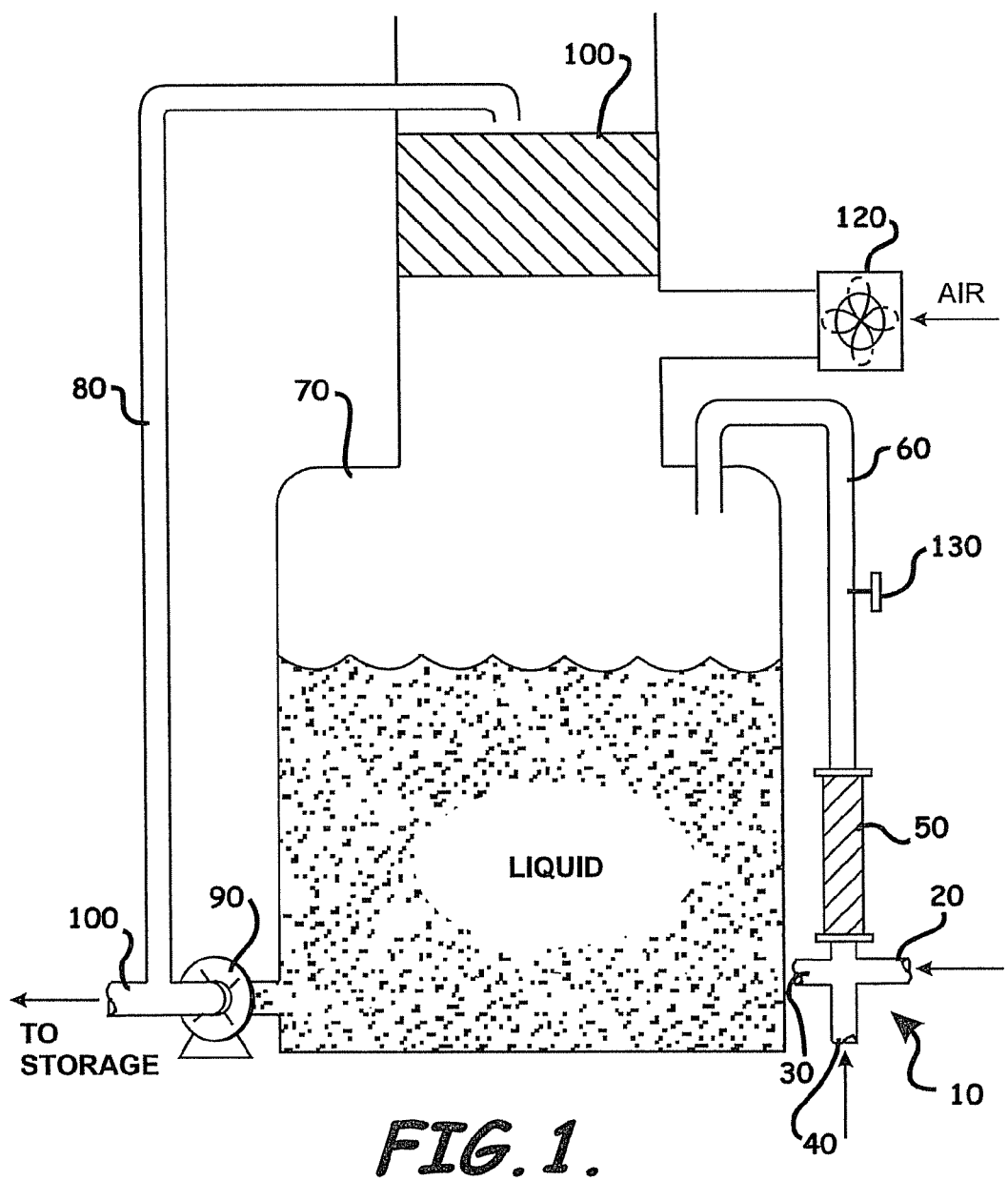
FIG. 1 is a cross-sectional side elevation of an apparatus which may be used in preparing the composition according to an embodiment of the present invention.

One embodiment of the reaction of the reaction mixture used in the novel compositions of this invention that provides bactericidal and nutritional activity comprises dissolving concentrated 99% crystalline phosphorous acid in a concentrated solution of phosphoric or super phosphoric acid to form a single super concentrate acid solution, which is capable of higher reaction temperatures with aqueous base metal hydroxide solution/hydroxide solutions, e.g., potassium hydroxide or potassium carbonate, in order to form high analysis potassium phosphates, potassium polyphosphates, potassium phosphites, and potassium polyphosphites and potassium phosphate phosphite copolymers.

An aspect of this invention that provides bactericidal activity when treating plants in an effective amount comprises an aqueous salicylate solution having salicylic acid reacted in an aqueous media with first with ammonium hydroxide and thereafter with potassium hydroxide, or in reverse order of hydroxide reaction.

Another aspect of this invention is a composition that provides fungicidal protection to plants and fertilizes plants when treated with an effective amount which composition comprises an aqueous blend of the above aqueous salicylate solution and an aqueous reaction mixture comprising potassium phosphates, potassium polyphosphate, potassium phosphites, and potassium polyphosphite and potassium phosphate phosphite copolymers.

Also, as part of this invention is a composition that provides superior fungicidal protection to plants when treated with an effective amount of the composition in which composition comprises an aqueous reaction mixture selected from the group consisting of potassium phosphates, potassium polyphosphate, potassium phosphites, potassium polyphosphite and potassium phosphate phosphite copolymers or combinations thereof, and an aqueous complexed potassium acetate solution.

The composition this contains a blending of:

(1) an aqueous salicylate solution component that comprises salicylic acid reacted in an aqueous media with ammonium hydroxide and potassium hydroxide. It is well known that ammonium hydroxide and potassium hydroxide cannot be mixed together; otherwise an undesirable reaction will occur. In mixing with salicylic acid, it is first mixed with ammonium hydroxide, allowed to react and thereafter followed by addition of potassium hydroxide, or vice versa; and (2) an aqueous reaction mixture component made from the reaction of: (a) an acid solution comprising about 10-50 parts phosphorous acid and about 50-90 parts phosphoric acid; and, b) aqueous potassium hydroxide or ammonium hydroxide where the ration of monovalent cations to phosphorous in mole ratios is between about 1:1 to about 2:1. The reaction mixture formed comprises potassium phosphates, potassium polyphosphate, potassium phosphites, and potassium polyphosphite and potassium phosphate phosphite copolymers. The aqueous reaction mixture component (2) is blended under pressure in a continuous system such as a pipe reactor and thereafter rapidly cooled, an example of which is presented as Example 11.

The aqueous salicylate solution (1) comprises 10-20% wt. salicylic acid substantially reacted in an aqueous media with a sufficient amount of between about 1 to 2 parts ammonium hydroxide and potassium hydroxide combined.

The above composition can readily be augmented by cold blending together urea and other nutrients thereby forming compositions that are stable, homogeneous and sprayable. These compositions are readily prepared by prescription for specific crops and specific situation and can be diluted with water if necessary when applied to plants.

The novel aqueous compositions synergistically and effectively feed crops, eliminate the deleterious effects of fungal diseases, bacterial diseases and insect damage and improve yields than if a pesticide and nutrient solution was used alone. After a period of time and upon exposure to the elements, the potassium polyphosphates and polyphosphites oxidize to provide fertilizer components to the crop, i.e., potassium and ortho-phosphorus. Furthermore, each of the novel aqueous compositions can be blended with components, such as, urea, nitrates or other ammonical compounds to provide a nitrogen component and also with effective amounts of secondary nutrients such as, calcium, magnesium, sulfur, and micronutrients, such as, boron, copper, iron, molybdenum, manganese and zinc to form a high quality fertilizer component. Stable clear and sprayable compositions are formed that have a relatively long shelf life.

The novel aqueous compositions can be cold blended with water for foliar spray application by the grower. The composition can be used in a concentrated form for metering and injection into a spray that is applied to a crop. Typically effective amounts are applied to crops depending on the crop and the problems associated with the crop that are corrected by the compositions of this invention.

The following are examples of synergistic treatment using my pesticide and nutrient solution combination Example 1

A test of the novel Dual Purpose Agricultural Composition (DPAC) of this invention was conducted in Martin County Florida in a 30 hectare block of Valencia oranges that had been abandoned and had no commercial value do to the sever incidence of Huanglongbing Citrus Greening Disease (HLB), which is transmitted by psyllids, which are small piercing sucking insects. HLB symptoms include small yellow leaves with a mottled or blotchy appearance and yellow veins exhibiting mineral deficiencies such as Manganese and Zinc, twig and branch dieback, sparse, small fruit that is abnormal in appearance and fails to color properly, thus the name greening, with aborted seeds and poor juice quality and finally rapid degeneration into a non-productive state. Mortality can occur within three years. Two different application rates of DPAC were applied in two partial sections of the block, seven liters per hectare and 14 liters per hectare. Micronutrients and other pest control materials were added to the tank mix and applied. Within four weeks of the initial application of DPAC, it was apparent that the all the trees began to recover as evidenced by new growth, on the barren twigs that had begun to die back. Within six months the recovery was readily obvious, trees began normal growth, and a total care program was restored.

Example 2

In an 800 hectare citrus grove located in Felda, Fla., six trees were diagnosed with *Xanthomonas citri* subsp. *Citri*., bacterial citrus canker, is a leaf, fruit, and stem blemishing disease, by the bacterial penetration of the stomatal pores. A 14 liter per pectate of DPAC was applied, together with other tank mix materials, and further spread and control of the canker was achieved. It was also noted that one of the trees had also been diagnosed with HLB and an inspection of the entire grove revealed a 90% HLB infection rate and treated with DPAC, from which no trees suffered mortality and the grove is returning to normal productivity.

Example 3

A commercial size test was undertaken in South Florida in order to test the efficacy of the NC of this invention in a citrus grove with 70% leaf loss rate, as compared to the recommended program of tree removal, in an adjoining citrus grove also infected with HLB. There were ultimately four treatments of 10 liters per hectare, along with micronutrients added to the tank mix, of DPAC. Within four months of initial treatment of DPAC, tree health and vigor was restored, as new leaf growth was observed throughout. The new canopy growth nearly doubled the tree size and a normal fruit crop was set. The grower reported that yields had returned to normal, while the adjoining grove, untreated with DPAC, continued to decline with tree removal continuing.

Example 4

A replicated research trial was conducted in order to ascertain which of the sprayed materials was achieving the results of examples one, two, and three, by a process of elimination conducted in seven different foliar spray regimes. It was determined that the DPAC of this invention could not be eliminated, in order to achieve control results of HLB, while other materials could be eliminated.

The aqueous reaction mixture component (2) is based on the "Detailed Description of the Preferred Embodiment" section of U.S. Pat. No. 8,221,516, the contents of which are hereby incorporated by reference.

The invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention of those skilled in the art. Other features and advantages of the invention will be apparent from the following detailed description and from the claims.

Apparatus for Manufacture of the Aqueous Reaction Mixture (2)

A preferred embodiment for the manufacture of component (2) of present invention employs the cross-pipe reactor described in U.S. Pat. No. 4,724,132 (the '132 patent) in combination with a down-stream mixer which is a static in-line mixer, the static in-line mixer can be extremely short or, in fact, the static inline mixer could comprise the entire length of the pipe 60 as shown, in which case the static in-line mixer would essentially deliver product into the receiving tank 70 and FIG. 1 would be modified to basically delete pipe 60. The primary criterion which would set the length of the static in-line mixer, if it is used, is to insure that reaction is substantially complete prior to the time the product enters the receiving tank 70 as shown in FIG. 1. Generally speaking, if the static in-line mixer (or some other mixer) is not used downstream the cross-pipe reactor the length of the pipe 60 should be increased to insure substantially complete reaction with a decrease in the length of pipe 60 if a static in-line mixer is used. The exact length of the static in-line mixer and/or the pipe 60 can easily be determined by standard chemical engineering practices.

The excellent mixing, polymerization and temperature obtained with the cross-pipe reactor creates a greater potassium hydroxide solution/acidulation surface area, and insures good conversion of the potassium compound(s) to polyphosphite salt. Acidulation is, of course, the process of adding acid, and generally the amount of mineral acid, phosphorous acid, is specified with respect to the amount of potassium hydroxide. This can easily be established by one skilled in the art.

As indicated, even more pronounced effects are obtained with the addition of the static in-line mixer down-stream from the cross-pipe reactor. A typical static in-line mixer useful in the present invention and, in fact, the one that has been used to date, is disclosed in U.S. Pat. No. 4,093,188 to Horner, hereby incorporated by reference. The particular static in-line mixer disclosed has stationary baffles providing sinuous, non-parallel spiraling flow paths to promote thorough and homogeneous intermixing of fluids. It is not mandatory to use that precise static in-line mixer and other static in-line mixers, also known as stationary baffle mixers or interfacial surface generators, can be used. For example, it is believed that stationary baffle mixers or interfacial surface generators as disclosed in U.S. Pat. Nos. 3,190,618; 3,620,506; 3,643,927; 3,652,061; 3,923,288; 3,947,939 and Reissue No. 28,072 could be used with equal success, and all of these patents are also incorporated by reference. Other mixers could likely be used instead of a static in-line mixer, for example, as can be appropriately selected by one skilled in the art from Chemical Engineers' Handbook, John H. Perry, Editor, Third Edition, McGraw-Hill Book Co., Inc., pp. 1195-1231

After the reactants have passed through the cross-pipe reactor 10, the mixer 50 and pipe 60, the reacted mixture is conveniently discharged into a receiving tank 70. Generally, it is preferable to substantially complete reaction prior to introduction of the product into the receiving tank 70. As one skilled in reaction kinetics will appreciate, there will be some slight amount of reaction in the receiving tank 70, but this is not of consequence if any reasonable amount of care is exercised over the process control, as would be understood by a chemical engineer. The discharge is usually above the level of the liquid in the receiving tank 70 in order to achieve faster flash cooling. If the discharge is below the liquid level, reducing to some degree the cooling capacity, the conversion ratio from metal hydroxide solution to salt is slightly improved. As will be appreciated by one skilled in the art, the use of a receiving tank is merely a convenient means to use a cool, large mass of product to inexpensively cool the product received from pipe 60. The composition should be cooled to approximately 90 F., or less, as rapidly as possible. Any conventional means could be used to achieve this cooling effect.

The determination and adjustment of optimum reaction parameters will be well within the skill of the chemical engineer. The product can be recirculated from receiving tank 70 through cooling means (not shown) via pump 90. If desired, some product can be sent to storage via line 100 but normally the greater volume is recirculated over a packed column 110 through which air is blown by fan 120 in order to cool the product prior to storage. Also, as one skilled in the art will appreciate, pumping means are provided throughout the system as needed; these are conventional and are not shown. Further, the skilled will recognize that, since a mineral acid is being used, conventional process equipment resistant to acidic conditions will be used, typically stainless steel.

Description of the Process

Figure 2:
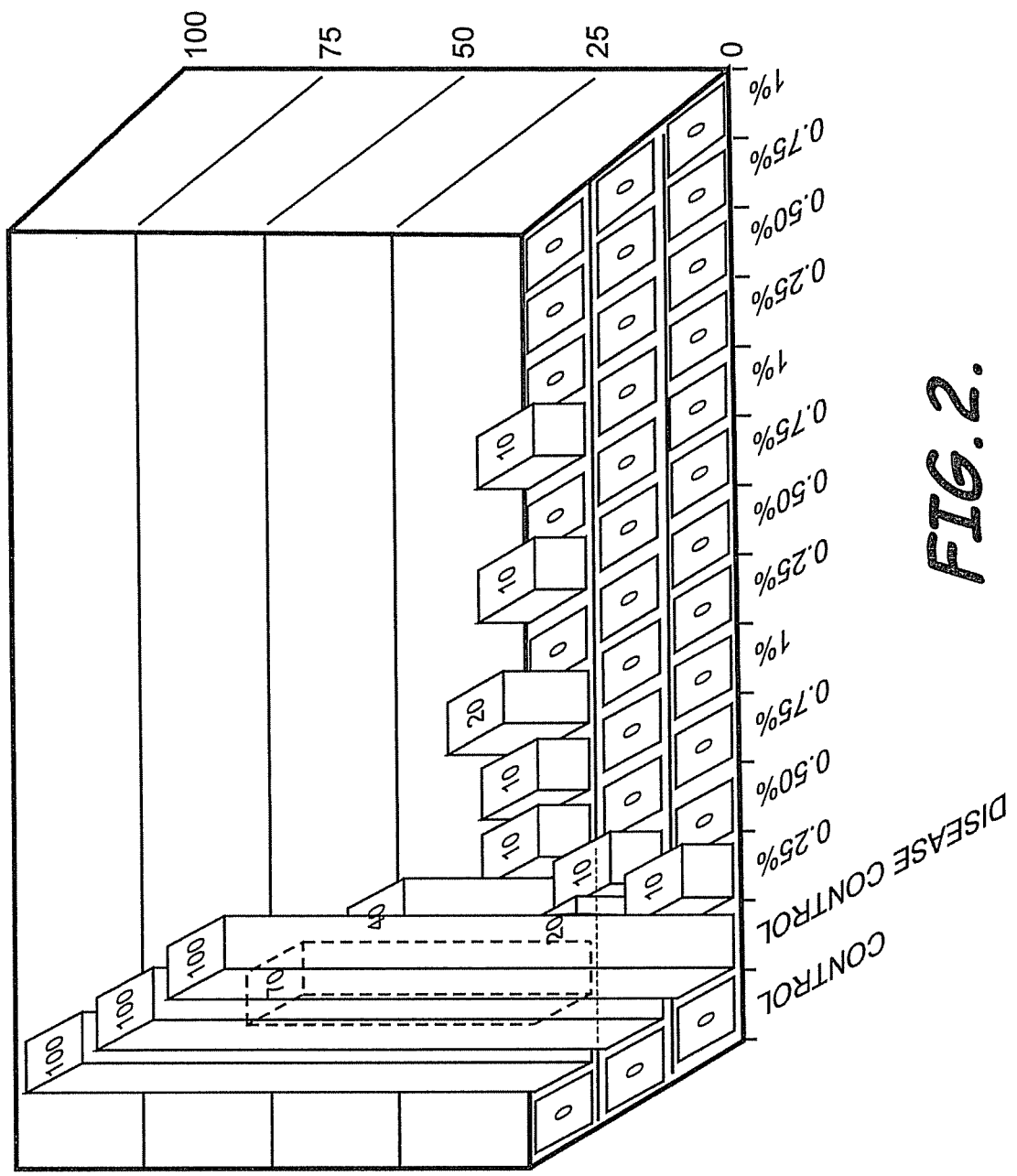
FIG. 2 is a graph showing activity of the present polyphosphite composition against some bacterial agents of plant disease.

Evidence of the makeup of the composition is found in NMR results of several samples and from chemical tests. Samples were prepared by the use of the apparatus of the present invention as shown in FIG. 1 and described below. NMR analysis was conducted by Process NMR Associates, LLC, using a Varian VXR 300-S Spectrometer. Spectra were recorded and the position of the peaks noted in terms of parts per million of field strength (ppm) relative to the standard inorganic phosphate peak. Simultaneously, the samples were examined for the hydrogen atom attached to the phosphorous atom using the transfer polarization technique. Concentration, different counter-ions, such as ammonium, sodium, or potassium can cause a small change in position of the peaks, therefore the exact position of the peaks in a given spectrum is not definitive. However, the relative position of one peak to another, such as phosphate versus phosphite, is useful. Potassium phosphite alone exhibits a single sharp peak for the $P^{31}$ atom and a correspondingly sharp peak in the transfer polarization spectrum for the $H^1$ atom that is attached to the P atom of all inorganic phosphites. To the contrary, no corresponding transfer polarization spectrum for $H^1$ is found for polyphosphites, which clearly indicates that there are no longer $H^1$ atoms attached to the phosphorus and that the starting material, $HPO_3^{-2}$, has been chemically changed. In addition, in confirmation of polymeric character, the peak is no longer sharp (half width of about 10 to 20 Hz) but very broad (half width of about 30 to 100 Hz). The breadth of such $P^{/1}$ NMR peaks, at a given field strength, is the result of the different positions of phosphorus atoms in the polymer and the different molecular weights of oligomers. Accordingly, each atom yields a signal indicating its unique environment and, since the signals are only slightly different, the result is a broader peak. In the case of phosphite and polyphosphite, the peak positions are very near each other and a broad peak can cover over a smaller narrower peak. Under the different conditions in the various examples of the present invention, the composition prepared may contain more or less potassium polyphosphite with the balance being simple potassium phosphite. However, several samples have been prepared by this invention that give no detectable response for P31-H1 in transfer polarization NMR analyses, thereby indicating that the samples are nearly 100% polymerized by P03-3, polyphosphite. Furthermore and analogous to polyphosphate chemistry, is has been found that the composition prepared by the present invention readily generates free acid when they are heated above ambient temperature thereby providing further confirmation of the proposed structure, as illustrated in FIG. 2. The amount of free acid continues to increase with time as the composition is held at an elevated temperature.

A most preferred embodiment in a continuous process of the present invention will be described with reference to the FIG. 1 and comprises a metal hydroxide solution, e.g., potassium hydroxide solution, as an aqueous solution reacted with a mineral acid, e.g., phosphorous acid, with water being added as necessary to adjust specific gravity. The metal hydroxide solution is pumped into port 20 of the cross-pipe tee 10, the mineral acid is pumped to port 30 and the water is pumped into port 40. Reaction begins on contact of the metal hydroxide solution and mineral acid and the mixture of the reactants is forced substantially immediately into the static in-line mixer 50 where reaction continues to occur. The rate of total feed is controlled so that the temperature as taken about midway up the pipe 60 above the in-line mixer 50 is maintained at a desired level, and preferably at about 300 degrees F.+/−0.50 degrees. Generally speaking, the reaction continues in the pipe 60. Since the reaction of the present invention is exothermic, external heat need not be supplied to the system. As a general practice, I simply measure the temperature about one-half way up the distance of the pipe 60 as shown in the FIG. 1 by temperature indicator 130. However, the temperature could easily be measured anywhere between the cross-pipe reactor and discharge into the receiving tank 70 as shown in FIG. 1. The ratio of the potassium hydroxide solution to phosphorous acid fed is adjusted to maintain product pH specification at the desired level, depending on the type of product being manufactured. The rate of water addition is controlled to maintain the desired product specific gravity. Product specific gravity is a relatively precise number and is typically set by the tolerances of fertilizer control laws. It can be freely selected by one skilled in the art. Various examples follow, including one example of a prior art batch process which is inadequate for use in the present invention.

Example 5

This example is a batch process and represents prior art methods, rather than a method of the present invention. It is presented here to show how the prior art is unable to achieve the results provided by the present invention.

Into a 5,000 ml stainless steel laboratory blend tank outfitted with an electric driven propeller-type mixer, a 2,000 gram batch of a 70% solution of phosphorous acid was dissolved and prepared from 1,414 grams of 99% white, crystalline phosphorous acid, into 586 grams of distilled water. A 70% solution of phosphorous acid is the normal concentration commercially available that is typically used in the production of phosphorous acid products. Heat was applied in order to keep the temperature at 70 degree. F. throughout the process and the mixture was stirred vigorously for approximately 10 minutes to obtain a uniform, clear solution of phosphorous acid. This solution was then poured off into a flak and stoppered. Of this solution, 918 grams was weighed into another flask and stoppered. 1,239 grams of 50% KOH was weighed and stored in a separate flask, both weighed products being of sufficient quantity in order to blend a 2,000 gram batch of a typical potassium phosphite product by the batch method, as known by those practicing in the art. There was a negative −157 gram imbalance of water which was expected to evaporate off as a result of the exothermic reaction. The 1,239 grams of KOH was poured into the above describe 5,000 ml tank, and agitation begun. At this point the laboratory ventilation system should be engaged and the technician should wear proper laboratory safety attire, including goggles, for handling hazardous materials. Then, the addition of the 918 grams of acid was started with continuous agitation. The rate of addition of acid was maintained as fast as possible but without causing vigorous boiling of the water. During the addition of the first 200 grams of acid, the batch began to boil vigorously, with the temperature reaching about 150 degree F. Upon cooling sufficiently, another 200 grams of acid was added slowly to the boiling point again continuously from the mixture. When most of the calculated amount of acid had been added, a very faint garlic-like odor was detectable, indicative of the formation of phosphine. The lab was immediately vacated until it was determined that the mixture had stopped boiling and that the lab had been properly ventilated. Personnel reentering the lab donned protective masks. It was not possible to complete the batch without exceeding about 130 degree F., without the material boiling over and out of the tank, and without the further risk of producing phosphine gas. The final pH was adjusted to 6.8 and the mixture was cooled in a water bath.

Example 6

This example describes the general process employed in the invention, in the temperature range as used also in examples 8 and 10. A run was carried out using equipment as shown in the above described crosspipe reactor including a special mixing device, i.e., an open cross-pipe reactor with a static in-line mixer, as disclosed in U.S. Pat. No. 4,093,188 to Horner. It is commercially available under the trade name STATA-TUBE and is a motionless mixture manufactured by TAH Industries, P.O. Box 178, Imlaystown, N.J. 08526, (2" L.D. times.96" length). In the Examples herein the runs were on a commercial scale using a cross tee reactor where the ports had an inner diameter of about 2 inches" and the pipe was about 96" in length having an inner diameter the same as the cross tee reactor ports. Obviously these dimensions are not restrictive and smaller and/or larger devices can be used. All process lines were stainless steel. Reactants were pumped into the cross-pipe injection ports as follows: a 50% solution of potassium hydroxide at a rate of approximately 21 gallons per minute (port 20), and 70% phosphorous acid at a rate of 15 gallons per minute (port 30). Water at a rate of approximately 3 gallons per minute was injected directly into the receiving tank, in order to attain the highest pipe temperature possible. The reaction product was simply flowed into a receiving tank above the liquid level for ease of operation. During the run frequent samples were taken from the tank for pH and specific gravity checks, and acid and water flows were adjusted to maintain these values at the desired levels, i.e., pH 6.8, specific gravity 1.45 (these values are the same in the following Examples unless indicated to the contrary). Acidulation and conversion were thus controlled. During the run the temperature at the midpoint of the pipe fluctuated from 260 degrees F. to 275 degrees F. The reactionary product entering the receiving tank was instantly cooled to about 115 degrees F. and was pumped to a finished product storage tank at a rate of approximately 33 gallons per minute. As a result of the evaporative cooling process taking place, voluminous steam plume was continuously emitted, and sampled for any trace of garlic like odor, and none was detected.

Example 7

Using the process of Example 6, the reactants were introduced at lower rates, sufficient to keep the temperature at the midpoint of the pipe below 200 degree F. and small portion of the resulting composition was immediately brought into the laboratory and packaged for rapid shipment to NMR Associates, LLC in Connecticut for testing by NMR. The NMR analysis revealed strong narrow peaks both for $P^{33}$ and $H^1$, which is indicative of the presence of the inorganic salt potassium phosphite.

Example 8

A run was carried out using the process of Example 6 where the temperature at the midpoint of the pipe was between 260 degree F. and 275 degree F. and a small portion was immediately brought into the laboratory and packaged for rapid shipment to NMR Associates, LLC in Connecticut for NMR analyses. The NMR analysis revealed a single broad strong peak for P.sup.31 and only small evidence of $H^1$ attached to $P^{31}$ under the polarization transfer test, which indicates that most of the inorganic potassium phosphite had been converted to polyphosphites but that some monophosphite remained.

Example 9

Figure 5:
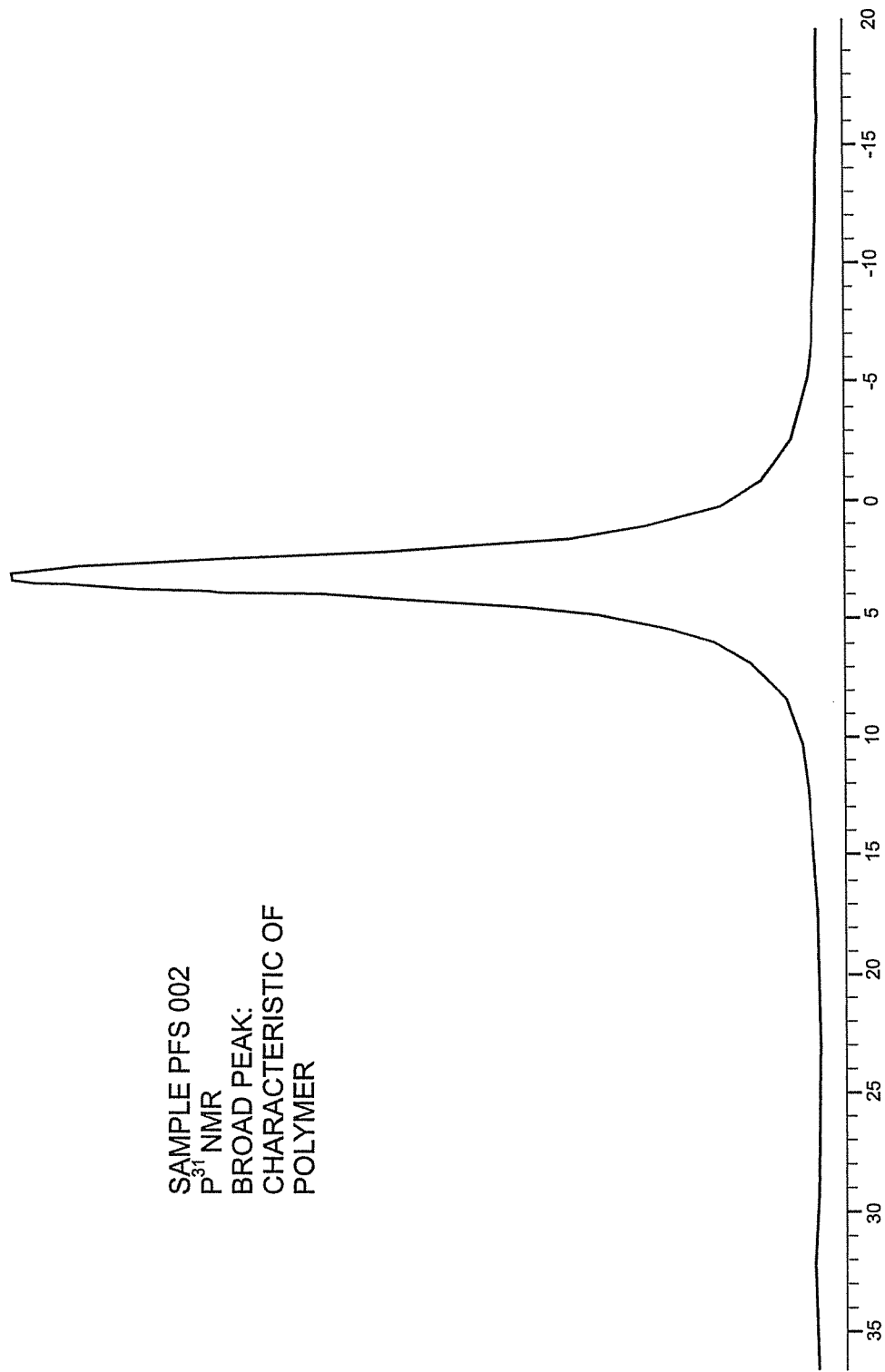
FIG. 5 NMR spectrum for $P^{31}$ for sample PFS 002, as described in Example 9; and, FIG. 6 is an NMR $H^1$ polarization transfer spectrum also for sample PFS 002.
Figure 6:
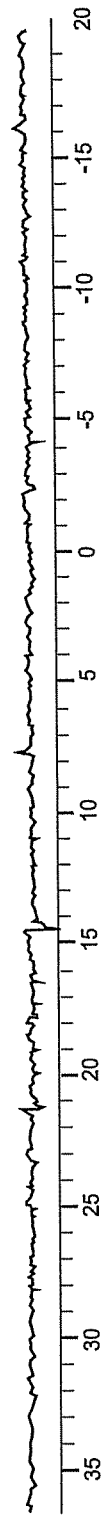

The process of Example 6 was followed, where the temperature at the midpoint of the pipe was maintained between about 270 degree F. and 285 degree F. A small portion was immediately brought into the laboratory and packaged for rapid shipment to NMR Associates, LLC in Connecticut for NMR analyses; this was labeled sample PFS 002. As shown in FIGS. 5-6, the NMR analysis revealed a single broad strong peak for $P^{31}$ but no evidence of $H^1$ attached to $P^{31}$ under the polarization transfer. This result indicates that essentially all of the inorganic potassium phosphite had been converted to polyphosphites.

Example 10

The process of Example 6 was carried out, but where the temperature at the midpoint of the pipe was maintained between about 260 degree F. and 275 degree F. Eight days later, a five-gallon sample was taken from the storage tank and portions were subjected to heat treatment at various temperatures as follows. The sample had a specific gravity of 1.46, a pH of 6.5, and the dry solids content was about 53%. The NMR showed a large narrow peak for $P^{31}$ and also a significant peak for $H^1$ under transfer polarization. A portion, 232 g., was heated over a period of 13 minutes in an open stainless steel pan until it boiled at 116 degree C. Weight measurements showed a loss of 53 g of water. Further hearing for a period of 15 minutes resulted in an additional loss of water of 33 g and the boiling point climbed to 145 degree C. The pH was 3. Another portion of 223 g of the original sample was heated in a similar manner but for less time so that the solution remained homogeneous. The pH was 4.

These experiments showed that free acid was being liberated upon heating, which is to be expected when hydrolysis of polyphosphite occurs. These data are consistent, indicating a sample containing a mixture of potassium phosphite (monomer) and polyphosphites.

Example 11

A mixture of phosphoric acid and phosphorous acid was prepared for use in the reactor of the present invention. Five hundred pounds (500 lb) of solid 99% phosphorous acid was dissolved in 1500 lb of 75% phosphoric acid in order to increase the concentration of reactants by reducing the amount of water, and so as to subsequently increase the reaction temperature. This acid mixture was reacted with a 50% solution of potassium hydroxide, the reaction expected to yield a mixture of potassium phosphate and potassium phosphite. The test run lasted approximately 3 hours.

Figure 3:
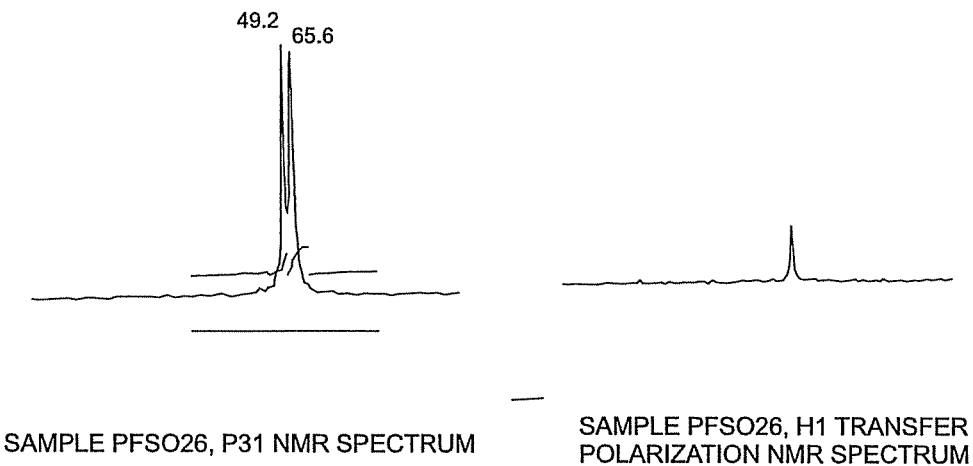
FIG. 3 NMR spectra for sample PFS 026, as described in example 11

The conditions of the reaction were varied over this period of time in order to study the effect of operational parameters. Five different conditions were studied. A small sample (7A) was withdrawn after each change in the reaction conditions after the system had stabilized. Sample number PFS026 was obtained when the reaction temperature was about 265 degree F., the pH was 8.22, the specific gravity was 1.475, and the sample temperature was 105 degree F. The NMR spectra for this sample are shown in FIG. 3. The $P^{31}$ spectrum shows two sharp peaks indicative of potassium phosphate and potassium phosphite. The $H^1$ spectrum for the hydrogen attached to the phosphorous atom, obtained by polarization transfer, confirms the presence potassium phosphite as expected.

Figure 4:
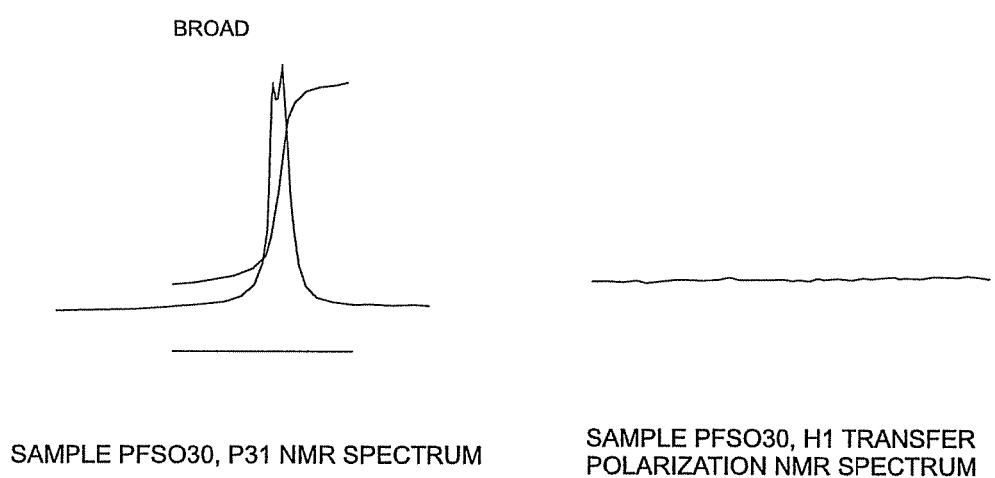
FIG. 4 NMR spectra for sample PFS 030, as described in example 11.

Sample PFS030 (7B) was obtained when the reaction temperature was about 300 degree F., the pH was 7.6, the specific gravity was 1.44, and the sample temperature was 100 degree F. The NMR spectra are shown in FIG. 4. Surprisingly, the $P^{/1}$ spectrum shows a very broad peak consistent with formation of polymer. The spectrum also shows small peaks at the top of the broad peak indicative of small amounts of unreacted potassium phosphate and potassium phosphite. Also surprisingly, the $H^1$ polarization transfer spectrum shows an absence of hydrogen atoms attached to the phosphorous atom and which clearly indicates that an unexpected chemical reaction has resulted in almost complete polymer formation.

Accordingly, in the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed is:

1. A method of fertilizing a plant, the method comprising applying to a plant an effective amount of a composition comprising a product of a salicylic acid, a potassium polyphosphite, a potassium phosphite, and a potassium phosphate.

2. The method of claim 1, wherein the composition further comprises a hydrolyzed potassium polyphosphite.

3. The method of claim 1, wherein the composition further comprises a potassium polyphosphate.

4. The method of claim 3, wherein the composition further comprises a hydrolyzed potassium polyphosphate.

5. The method of claim 1, wherein the composition further comprises a potassium polyphosphate and a phosphate/phosphite copolymer.

6. The method of claim 1, wherein the plant is infected with at least one of bacterial wilt infection, citrus canker disease, and citrus greening disease.

7. The method of claim 1, wherein the salicylic acid is a salicylate.

8. A plant fertilizer composition comprising a salicylic acid based product, a potassium polyphosphite, a potassium phosphite, and a potassium phosphate.

9. The plant fertilizer composition of claim 8, further comprising a hydrolyzed potassium polyphosphite.

10. The plant fertilizer composition of claim 8, further comprising a potassium polyphosphate.

11. The plant fertilizer composition of claim 10, further comprising a hydrolyzed potassium polyphosphate.

12. The plant fertilizer composition of claim 8, further comprising a potassium polyphosphate and a phosphate/phosphite copolymer.

13. The plant fertilizer composition of claim 8, wherein the salicylic acid based product is a salicylate.

14. A method of fertilizing a plant, the method comprising applying to a plant an effective amount of a composition comprising a potassium phosphate and a potassium phosphite, the composition being prepared by reacting salicylic acid, ammonium hydroxide, potassium hydroxide and/or potassium carbonate, phosphoric acid, and phosphorous acid.

15. The method of claim 14, wherein the composition comprises a salicylic acid based product and a potassium polyphosphite.

16. The method of claim 15, wherein the salicylic acid based product is a salicylate.

17. The method of claim 14, wherein the composition comprises a hydrolyzed potassium polyphosphite.

18. The method of claim 14, wherein the composition comprises a potassium polyphosphate.

19. The method of claim 18, wherein the composition comprises a hydrolyzed potassium polyphosphate.

20. The method of claim 14, wherein the composition comprises a potassium polyphosphate and a phosphate/phosphite copolymer.

21. The method of claim 14, wherein the plant is infected with at least one of bacterial wilt infection, citrus canker disease, and citrus greening disease.

* * * * *